United States Patent
Sinha et al.

(10) Patent No.: US 12,109,050 B2
(45) Date of Patent: *Oct. 8, 2024

(54) METHOD AND SYSTEM FOR ACQUIRING DATA FOR ASSESSMENT OF CARDIOVASCULAR DISEASE

(71) Applicant: Riva Health, Inc., Burlingame, CA (US)

(72) Inventors: Tuhin Sinha, Burlingame, CA (US); Ian Eslick, Burlingame, CA (US); Alan Leggitt, Burlingame, CA (US)

(73) Assignee: Riva Health, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/522,806

(22) Filed: Nov. 29, 2023

(65) Prior Publication Data

US 2024/0099667 A1   Mar. 28, 2024

Related U.S. Application Data

(60) Division of application No. 17/588,080, filed on Jan. 28, 2022, now Pat. No. 11,872,061, which is a
(Continued)

(51) Int. Cl.
*A61B 5/02* (2006.01)
*A61B 5/00* (2006.01)
(Continued)

(52) U.S. Cl.
CPC .......... *A61B 5/7275* (2013.01); *A61B 5/0077* (2013.01); *A61B 5/02427* (2013.01);
(Continued)

(58) Field of Classification Search
CPC .............. A61B 5/0077; A61B 5/02108; A61B 5/02427; A61B 5/02438; A61B 5/4812;
(Continued)

(56) References Cited

U.S. PATENT DOCUMENTS 5,649,543 A   7/1997  Hosaka et al.
6,337,629 B1  1/2002  Bader
(Continued)

FOREIGN PATENT DOCUMENTS

CN   103826532 A   5/2014
CN   104337509 A   2/2015
(Continued)

OTHER PUBLICATIONS

"Clinical Validation of Tele-stethoscope System Digital", https://clinicaltrials.gov/ct2/show/study/NCT03596541, first posted Jul. 24, 2018.
(Continued)

*Primary Examiner* — Amanda K Hulbert
(74) *Attorney, Agent, or Firm* — Jeffrey Schox; Annie Imbrie-Moore

(57) ABSTRACT

A method and system for acquiring data for assessment of cardiovascular disease, the method comprising one or more of: manipulating one or more hardware aspects of the photoplethysmography data acquisition system(s) implementing the method; manipulating or providing user experience/user interface (UX/UI) aspects of the system(s) implementing the method; acquiring, processing, and deriving insights population specific data; accounting for or controlling sampling site variability; and using other suitable sources of data in order to generate high quality data for characterization, assessment, and management of cardiovascular disease.

4 Claims, 8 Drawing Sheets

Related U.S. Application Data continuation of application No. 16/538,361, filed on Aug. 12, 2019, now Pat. No. 11,266,356, which is a continuation of application No. 15/357,621, filed on Nov. 21, 2016, now Pat. No. 10,420,515, which is a continuation-in-part of application No. 15/183,285, filed on Jun. 15, 2016, now Pat. No. 10,420,475.

(60) Provisional application No. 62/175,971, filed on Jun. 15, 2015, provisional application No. 62/257,888, filed on Nov. 20, 2015.

(51) Int. Cl.

| | |
|---|---|
| A61B 5/024 | (2006.01) |
| G06N 20/00 | (2019.01) |
| G16H 20/10 | (2018.01) |
| G16H 20/70 | (2018.01) |
| G16H 30/40 | (2018.01) |
| G16H 40/63 | (2018.01) |
| G16H 50/20 | (2018.01) |
| G16H 50/30 | (2018.01) |
| A61B 5/0205 | (2006.01) |
| A61B 5/021 | (2006.01) |

(52) U.S. Cl.
CPC ........ *A61B 5/02438* (2013.01); *A61B 5/7221* (2013.01); *G06N 20/00* (2019.01); *G16H 20/10* (2018.01); *G16H 20/70* (2018.01); *G16H 30/40* (2018.01); *G16H 40/63* (2018.01); *G16H 50/20* (2018.01); *G16H 50/30* (2018.01); *A61B 5/02055* (2013.01); *A61B 5/02108* (2013.01); *A61B 5/4812* (2013.01); *A61B 5/6826* (2013.01); *A61B 5/6843* (2013.01); *A61B 5/7239* (2013.01); *A61B 5/7264* (2013.01); *A61B 2576/00* (2013.01)

(58) Field of Classification Search
CPC .............. A61B 5/7264; A61B 2576/00; A61B 5/02055; A61B 5/02116; A61B 5/02405; A61B 5/02416; A61B 5/4857; A61B 5/6826; A61B 5/6843; A61B 5/6898; A61B 5/7221; A61B 5/7239; A61B 5/7275; G06F 19/30; G06N 20/00; G06N 7/005; G01R 17/105; G01R 19/25; G01R 27/02; G16H 20/10; G16H 20/70; G16H 30/40; G16H 40/63; G16H 50/20; G16H 50/30; H03M 1/46; H03M 1/742; H03M 3/00; H03M 3/04; H03M 3/458
See application file for complete search history.

(56) References Cited

U.S. PATENT DOCUMENTS

| | | | |
|---|---|---|---|
| 6,475,153 B1 | 11/2002 | Khair et al. | |
| 6,993,377 B2 | 1/2006 | Flick et al. | |
| 7,286,875 B1 | 10/2007 | Park et al. | |
| 7,787,946 B2 | 8/2010 | Stahmann et al. | |
| 8,239,010 B2 | 8/2012 | Banet et al. | |
| 8,761,853 B2 | 6/2014 | Thaveeprungsriporn et al. | |
| 9,665,213 B2 | 5/2017 | Christman et al. | |
| 10,420,475 B2 | 9/2019 | Sinha et al. | |
| 10,420,515 B2 | 9/2019 | Sinha et al. | |
| 11,266,356 B2 * | 3/2022 | Sinha .................. | G16H 50/30 |
| 11,324,411 B2 | 5/2022 | Sinha et al. | |
| 2003/0163057 A1 | 8/2003 | Flick et al. | |
| 2008/0045818 A1 | 2/2008 | Wood et al. | |
| 2009/0326386 A1 | 12/2009 | Sethi et al. | |
| 2010/0168589 A1 | 7/2010 | Banet et al. | |
| 2011/0066051 A1 | 3/2011 | Moon et al. | |
| 2011/0077531 A1 | 3/2011 | Addison et al. | |
| 2011/0224564 A1 | 9/2011 | Moon et al. | |
| 2012/0029320 A1 | 2/2012 | Watson et al. | |
| 2012/0179011 A1 | 7/2012 | Moon et al. | |
| 2012/0190947 A1 | 7/2012 | Chon et al. | |
| 2013/0276785 A1 | 10/2013 | Melker et al. | |
| 2013/0310656 A1 | 11/2013 | Lim et al. | |
| 2013/0345568 A1 | 12/2013 | Mestha et al. | |
| 2014/0003454 A1 | 1/2014 | Kaemmerer et al. | |
| 2014/0275854 A1 | 9/2014 | Venkatraman et al. | |
| 2014/0278220 A1 | 9/2014 | Yuen | |
| 2014/0303454 A1 | 10/2014 | Clifton et al. | |
| 2015/0037937 A1 | 2/2015 | Park et al. | |
| 2015/0080746 A1 | 3/2015 | Bleich et al. | |
| 2015/0182132 A1 | 7/2015 | Harris et al. | |
| 2015/0313484 A1 | 11/2015 | Burg et al. | |
| 2015/0324977 A1 | 11/2015 | Magrath et al. | |
| 2015/0379370 A1 | 12/2015 | Clifton et al. | |
| 2016/0058375 A1 | 3/2016 | Rothkopf | |
| 2016/0256117 A1 | 9/2016 | Baik et al. | |
| 2016/0287110 A1 | 10/2016 | Morris et al. | |
| 2016/0302674 A1 | 10/2016 | Moyer et al. | |
| 2016/0360980 A1 | 12/2016 | Sinha et al. | |
| 2017/0007137 A1 | 1/2017 | Hong et al. | |
| 2017/0071516 A1 | 3/2017 | Bhagat et al. | |
| 2017/0079533 A1 | 3/2017 | Robinson et al. | |
| 2018/0146865 A1 | 5/2018 | Ortlepp | |
| 2018/0184983 A1 | 7/2018 | Petersen et al. | |
| 2019/0059753 A1 | 2/2019 | Chen et al. | |
| 2019/0175120 A1 | 6/2019 | Huang | |
| 2019/0357855 A1 | 11/2019 | Sinha et al. | |
| 2020/0330042 A1 | 10/2020 | Shiue et al. | |
| 2021/0212582 A1 | 7/2021 | Fathieh et al. | |
| 2022/0133158 A1 | 5/2022 | Jones et al. | |
| 2022/0133162 A1 | 5/2022 | Jones et al. | |
| 2022/0133241 A1 | 5/2022 | Jones et al. | |
| 2023/0074082 A1 | 3/2023 | Sinha et al. | |

FOREIGN PATENT DOCUMENTS

| | | |
|---|---|---|
| EP | 2992820 A2 | 3/2016 |
| KR | 20160028093 A | 3/2016 |
| WO | 2014022906 A1 | 2/2014 |
| WO | 2015193551 A1 | 12/2015 |
| WO | 2017152098 A1 | 9/2017 |

OTHER PUBLICATIONS

"National Institute of Health and Nutrition Examination Survey (NHANES)", Health Tech/Blood Pressure Procedures Manual, May 2009.

"Non-invasive sphygmomanometers—Part 2: Clinical investigation of intermittent automated measurement type", International Standard, ISO 81060-2, Third edition Nov. 2018.

Elgendi, Mohamed, "Merging digital medicine and economics: Two moving averages unlock biosignals for better health", Diseases 6.1 (2018): 6. (Year: 2018).

Lai, Lillian S.W., et al., "Computerized Automatic Diagnosis of Innocent and Pathologic Murmurs in Pediatrics: A Pilot Study", Congenital Heart Dis. 2016;11:386-395.

Lee, Han-Wook, et al., "he periodic moving average filter for removing motion artifacts from PPG signals", International Journal ofControl, Automation, and Systems 5.6 (2007): 701-706. (Year: 2007).

Perpetuini, David, et al., "Multi-site photoplethysmographic and electrocardiogram for arterial stiffness and cardiovascular status assessment", Sensors 19.24 (2019): 5570. (Year: 2019).

Rojano, Juan F., "Singular value decomposition of the time-frequency distribution of PPG signals for motion artifact reduction", Int. J. Signal Process. Syst 4.6 (2016): 475-482. (Year: 2016).

Scholze, A., et al., "Increased arterial vascular tone during the night in patients with essential hypertension", Journal of Human Hypertension (2007) 21, 60-67. published online Oct. 5. [retrieved on Aug. 22, 2016] retrieved from the Internet : http://www.nature.com.

(56) References Cited

OTHER PUBLICATIONS

Sinha, Tuhin, et al., "System and Method for Determining Data Quality for Cardiovascular Parameter Determination", U.S. Appl. No. 18/383,166, filed Oct. 24, 2023.

Stergiou, George S., et al., "A Universal Standard for the Validation of Blood Pressure Measuring Devices", Hypertension, Mar. 2018;71(3):368-374, doi: 10.1161/HYPERTENSIONAHA.117. 10237. Epub Jan. 31, 2018.

Stergiou, George S., et al., "Validation protocols for blood pressure measuring devices in the 21st century", J Clin Hypertens. 2018;20:1096-1099.

Sugita, Norihiro, et al., "Techniques for estimating blood pressure variation using video images", 37th Annual International Conference of the IEEE Engineering in Medicine and Biology Society (EMBC) Aug. 29, 2015.

Trafton, Anne, "In the blink of an eye, MIT neuroscientists find the brain can identify images seen for an as little as 13 milliseconds", MIT News, Jan. 16, 2014.

Vadrevu, Simhadri, et al., "A robust pulse onset and peak detection method for automated PPG signal analysis system", IEEE Transactions on Instrumentation and Measurement 68.3 (2018): 807-817. (Year: 2018).

Wang, Lu, et al., "Multi-Gaussian fitting for pulse waveform using weighted least squares and multi-criteria decision making method", Computers in biology and medicine 43.11 (2013): 1661-1672. (Year: 2013).

Wu, Hongiun, et al., "A New Automatic blood pressure kit auscultates for accurate reading with a smartphone", Medicine (2016) 95:32.

\* cited by examiner

METHOD AND SYSTEM FOR ACQUIRING DATA FOR ASSESSMENT OF CARDIOVASCULAR DISEASE

CROSS-REFERENCE TO RELATED APPLICATIONS

This application is a divisional of U.S. application Ser. No. 17/588,080, filed 28 Jan. 2022, which is a continuation of U.S. application Ser. No. 16/538,361, filed 12 Aug. 2019, which is a continuation of U.S. application Ser. No. 15/357,621, filed 21 Nov. 2016, which is a continuation-in-part of U.S. application Ser. No. 15/183,285 filed 15 Jun. 2016, which claims the benefit of U.S. Provisional Application Ser. No. 62/175,971 filed 15 Jun. 2015, each of which are incorporated herein in their entirety by this reference.

U.S. application Ser. No. 15/357,621, filed 21 Nov. 2016 also claims the benefit of U.S. Provisional Application Ser. No. 62/257,888 filed 20 Nov. 2015, which is incorporated in its entirety herein by this reference.

TECHNICAL FIELD

This invention relates generally to the field of cardiovascular disease, and more specifically to a new and useful method and system for acquiring data for assessment and management of cardiovascular disease.

BACKGROUND

The total market size for cardiovascular disease (CVD) is approximately $600 billion, with one in three American adults suffering from one or more types of CVD. It has been estimated that the total costs of hypertension (HTN) alone exceed $90 billion, including costs for medications, unnecessary complications, emergency department visits, and hospitalization. In most cases, patients with HTN are co-morbid with other conditions, and HTN can indicate risk of aneurysms, heart attack, stroke kidney failure, metabolic syndrome, heart failure, and other types of CVD; thus, CVD is a tremendous burden to the healthcare system.

Unfortunately, current standards of CVD assessment and management are fraught with inefficiencies, and technologies for assessing, managing, and treating CVD are substantially outdated. In particular, patient access between office visits/hospitalizations is limited or non-existent, which is exacerbated by the declining supply of general cardiologists and the growing demand of cardiology patients. Additional factors contribute to deficiencies in current methods of providing remote management of patients with CVD-related conditions. There is thus a need in the field of cardiovascular disease to create a new and useful method and system for acquiring data for assessment and management of cardiovascular disease. This invention provides such a new and useful method and system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Method

As described in more detail below, embodiments of the method 100 generally include blocks or steps configured to control, modulate, or process information derived from one or more of: hardware aspects of the data acquisition system (s) implementing the method; user experience/user interface (UX/UI) aspects of the system(s) implementing the method; population specific data; sampling site variability; and other suitable sources in order to generate high quality data for characterization, assessment, and management of cardiovascular disease. The method 100 can function to process one or more data streams in order to provide accurate, real-time (or near real-time) beat-by-beat cardiac biomarker estimation analyses and insights using a camera-based acquisition system (e.g., of a mobile computing device).

Figure 1A:
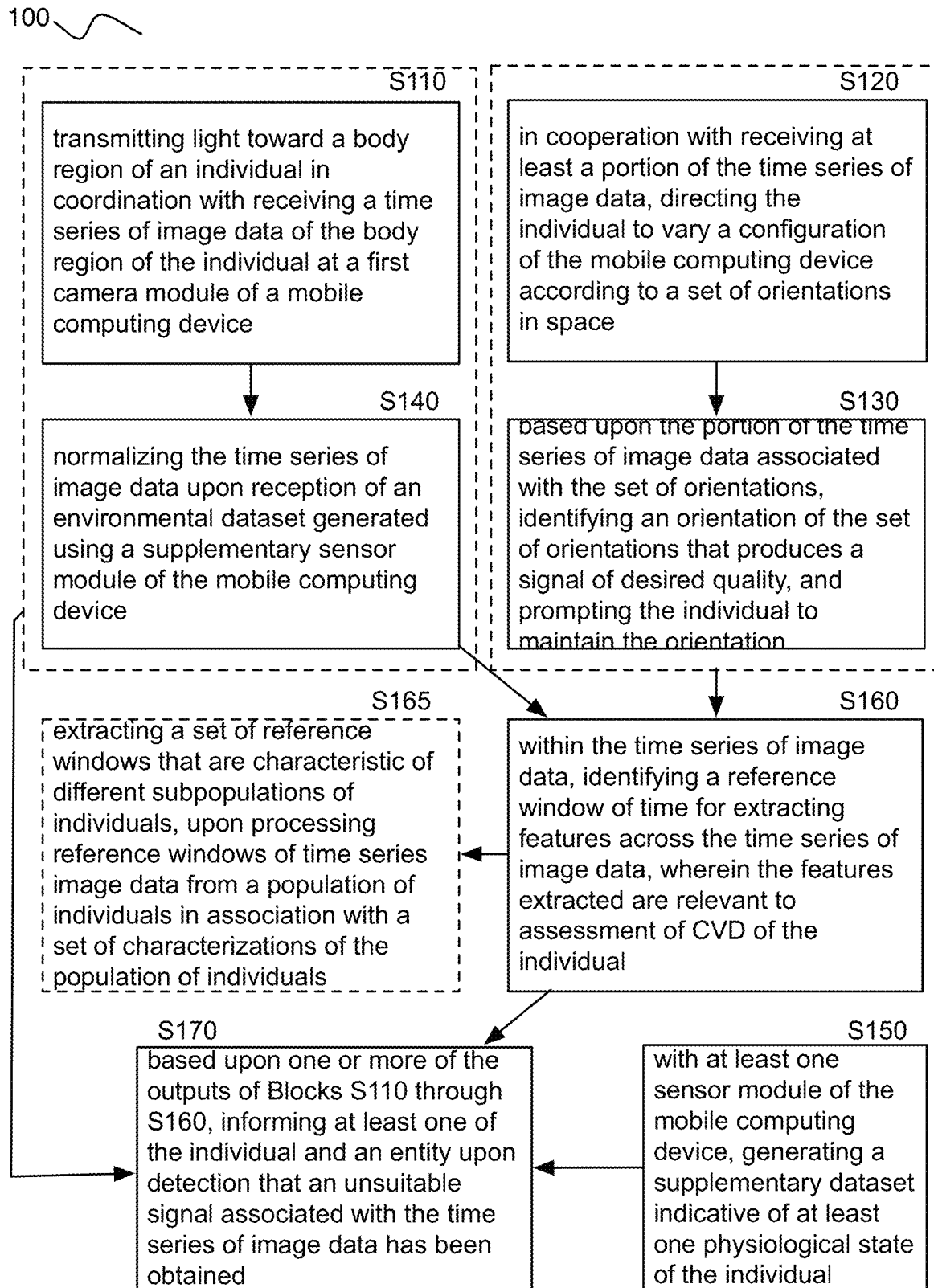
FIG. 1A depicts an embodiment of a method for acquiring data for assessment and management of cardiovascular health.

Thus, as shown in FIG. 1A, an embodiment of a method 100 for acquiring data for assessment of CVD in an individual can include one or more of: transmitting light toward a body region of an individual in coordination with receiving a time series of image data of the body region of the individual at a first camera module of a mobile computing device S110; in cooperation with receiving at least a portion of the time series of image data, directing the individual to vary a configuration of the mobile computing device according to a set of orientations in space S120; based upon the portion of the time series of image data associated with the set of orientations, identifying an orientation of the set of orientations that produces a signal of desired quality, and prompting the individual to maintain the orientation during generation of the time series of image data S130; normalizing the time series of image data upon reception of an environmental dataset generated using a supplementary sensor module of the mobile computing device S140; with at least one sensor module of the mobile computing device, generating a supplementary dataset indicative of at least one physiological state of the individual S150; within the time series of image data, identifying a reference window of time for extracting features across the time series of image data, wherein the features extracted are relevant to assessment of CVD of the individual S160; and based upon one or more of the outputs of Blocks S110 through S160, informing at least one of the individual and an entity upon detection that an unsuitable signal associated with the time series of image data has been obtained S170.

In some variations, the method 100 can additionally or alternatively include extracting a set of reference windows that are characteristic of different subpopulations of individuals, upon processing reference windows of time series image data from a population of individuals in association with a set of characterizations of the population of individuals S165, which can function to generate "biomarkers" that can be used to diagnose, characterize, or facilitate data processing for different populations or/subpopulations of individuals, as described in more detail below.

As noted above, the method 100 functions to control, modulate, or process information derived from one or more of: hardware aspects of the data acquisition system(s) implementing the method; user experience/user interface (UX/UI) aspects of the system(s) implementing the method; population specific data; sampling site variability; and other suitable sources in order to generate high quality data for characterization, assessment, and management of cardiovascular disease. Preferably, the method 100 provides high quality photoplethysmography (PPG) data from which physiological parameters conducive to the assessment of hypertension in an individual can be extracted, such that the method 100 can facilitate assessment of hypertension (and comorbid conditions) for a patient who is remote from a clinical environment. For instance, data generated using embodiments, variations, and examples of the method 100 can be used to generate high quality data from which one or more of: heart beat-associated parameters (e.g., heart rate, heart rate variability, QRS complex components, etc.), blood pressure-associated parameters (e.g., systolic blood pressure, diastolic blood pressure, blood pressure variability, etc.), parameters associated with atherosclerosis, parameters associated with pulse wave transit, and any other suitable parameter(s) relevant to assessment of CVD. However, the method 100 can alternatively provide high quality data derived from any other suitable sensor modules, for characterization of any other suitable condition associated with CVD.

As such, the method 100 can be implemented in coordination with methods involving one or more of: receiving a time series of image data while ensuring that signal quality is high during capture (e.g., in relation to finger pressure and other factors described herein); using pixel analysis and other processing steps on the time series of image data; detecting and/or accommodating changes in user aspects (e.g., finger placement, finger pressure, physiological changes, etc.) during capture of the time series of image data; extracting features of interest from the time series of image data and processing the features in analyses of the individual and/or a population of individuals; estimating biomarker characteristics from the analyses; and determining one or more risk factors associated with cardiovascular health of individuals being examined according to the method 100. The method 100 can thus be implemented in coordination with one or more embodiments, variations, and examples of which are described in U.S. application Ser. No. 15/183,285 titled "Method and System for Cardiovascular Disease Assessment and Management" and filed on 15 Jun. 2016, which is incorporated herein in its entirety by this reference.

In relation to remote assessment of a patient, the method 100 is preferably implemented, at least in part, using a mobile computing device of the patient, such that the patient can be remote from a clinical setting (e.g., hospital, clinic, etc.) during extraction of clinically-relevant parameters associated with CVD or general cardiovascular health. In a specific implementation of the method 100 and system 200, an individual can hold a smartphone, position his/her finger over a camera lens of the smartphone, while the individual's finger is illuminated with a lighting system (e.g., LED flash) of the smartphone. Then, the method 100 can be used to perform continuous acquisition of image/video data while the individual holds the smartphone, in a capture session. Multiple capture sessions can be used to adapt workflows for estimating, correcting, and/or determining one or more cardiac biomarkers according to the method 100, across sessions for an individual and/or across sessions for multiple individuals. While some embodiments of the method 100 implement a mobile computing device, alternative variations of the method 100 can additionally or alternatively implement any other suitable medical device system configured to capture image data from and/or transmit light toward a body region of an individual (e.g., using a camera module and/or illumination module of a wearable device coupled the body region of the individual). In such variations, the wearable device can be one or more of: head-mounted, wrist coupled, forearm coupled, and coupled to any other suitable body region of the individual.

As such, the method 100 is preferably implemented, at least in part, at an embodiment, variation, or example of the system 200 described in Section 2 below; however, the method 100 can additionally or alternatively be implemented using any other suitable system(s), some embodiments, variations, and examples of which are described in U.S. application Ser. No. 15/183,285 titled "Method and System for Cardiovascular Disease Assessment and Management" and filed on 15 Jun. 2016, which is herein incorporated in its entirety by this reference.

1.1 Method and System Benefits

In specific examples, the method 100 and/or system 200 can provide several benefits over conventional methodologies for determining and cardiovascular parameters for managing cardiovascular disease. In specific examples, the method 100 and/or system 200 can perform one or more of the following:

First, the technology can provide a convenient, frictionless user experience that improves signal quality, feature extraction and processing, and outputs configured to detect changes in cardiovascular health of individuals and/or improve cardiovascular health of individuals. For example, rather than requiring an external device usually coupled to a smart phone, portions of the method 100 can be implemented with consumer smartphone devices (or other mobile computing devices). In specific examples, cardiovascular parameters and cardiovascular risks can be determined based on image data captured from a smartphone camera by a individual. Such implementation can reduce the need for individual-specific a priori calibration using statistical modeling of population data across demographics and disease. In variations, the method 200 can be performed without supplementary electrocardiogram datasets, circumventing the need for an ECG biosignal detector.

Second, the technology can improve upon existing sensor technology by improving specificity in ascertaining and managing cardiovascular disease burden in individuals. Such specificity can aid in providing targeted therapies to patients. For example, improvements in specificity can be ascertained in determining cardiovascular parameters such as: heart rate, heart rate variability, blood pressure, blood pressure variability, measures of blood vessel stiffness, measures indicative of atherosclerosis, and/or other relevant cardiovascular parameters indicative of cardiovascular risk.

Third, the technology can leverage imaged-derived signal processing technologies to specifically determine and assess cardiovascular parameters in order to enable automatic facilitation of therapy provision, including: modulating medication provision, automatically adjusting environmental aspects of the individual to promote health of the individual, providing tailored medical recommendations, facilitating digital communications between patients and care providers, and/or any suitable therapy provision for managing cardiovascular disease.

Fourth, the technology can confer improvements to the technological areas of at least biosensors, leveraging mobile computing device technology to determine cardiovascular parameters, and digital management of cardiovascular disease. Such improvements can be conferred through, for example, the facilitation of self- and/or remote-cardiovascular health monitoring, enabling a more convenient individual experience for improving individual adherence. Further, a frictionless user experience can be provided while maintaining a sufficient level of specificity of physiological monitoring of cardiovascular disease-related health states, in order to enable automatic, tailored therapy provision.

Fifth, the technology can confer improvements in a mobile computing device itself that is implementing one or more portions of the method 200, as the mobile computing device can be transformed into a biosignal detector with high specificity in determining relevant cardiovascular parameters and/or managing cardiovascular disease. In examples, the technology can enable cardiovascular parameter evaluation using fewer sources of data (e.g., without electrocardiogram data), thus requiring computing systems to process fewer types of data.

Sixth, the technology can provide technical solutions necessarily rooted in computer technology (e.g., leveraging a mobile computing device to capture image data; transforming image data to different states such as raw and processed biosignals used for determining cardiovascular status of individuals; automatically facilitating therapy provision based on such data, etc.) to overcome issues specifically arising with computer technology (e.g., how to leverage mobile computing systems for cardiovascular management in a user-frictionless manner; how to allow computer systems to determine certain cardiovascular parameters using fewer types of data; how to facilitate digital communication of time-sensitive data amongst a system of computing systems, in order to enable automatic therapy provision in situations where the patient is at risk, etc.).

The technology can, however, provide any other suitable benefit(s) in the context of using non-generalized computer systems for digital health applications.

1.2 Method—Data Acquisition, Processing, and Hardware Control

Block S110 recites: transmitting light toward a body region of an individual in coordination with receiving a time series of image data of the body region of the individual at a first camera module of a mobile computing device. Block S110 functions to generate light absorption data from a body region of the individual, wherein the light absorption data can provide non-invasive determination of parameters associated with different states of CVD, HTN, and/or any other suitable biomarkers indicative of cardiovascular health. Block S110 can thus function to generate raw photoplethysmography (PPG) data for monitoring of perfusion of blood to the dermis and subcutaneous tissue of the skin of the individual, over a duration of time and in a non-clinical setting.

Figure 2:
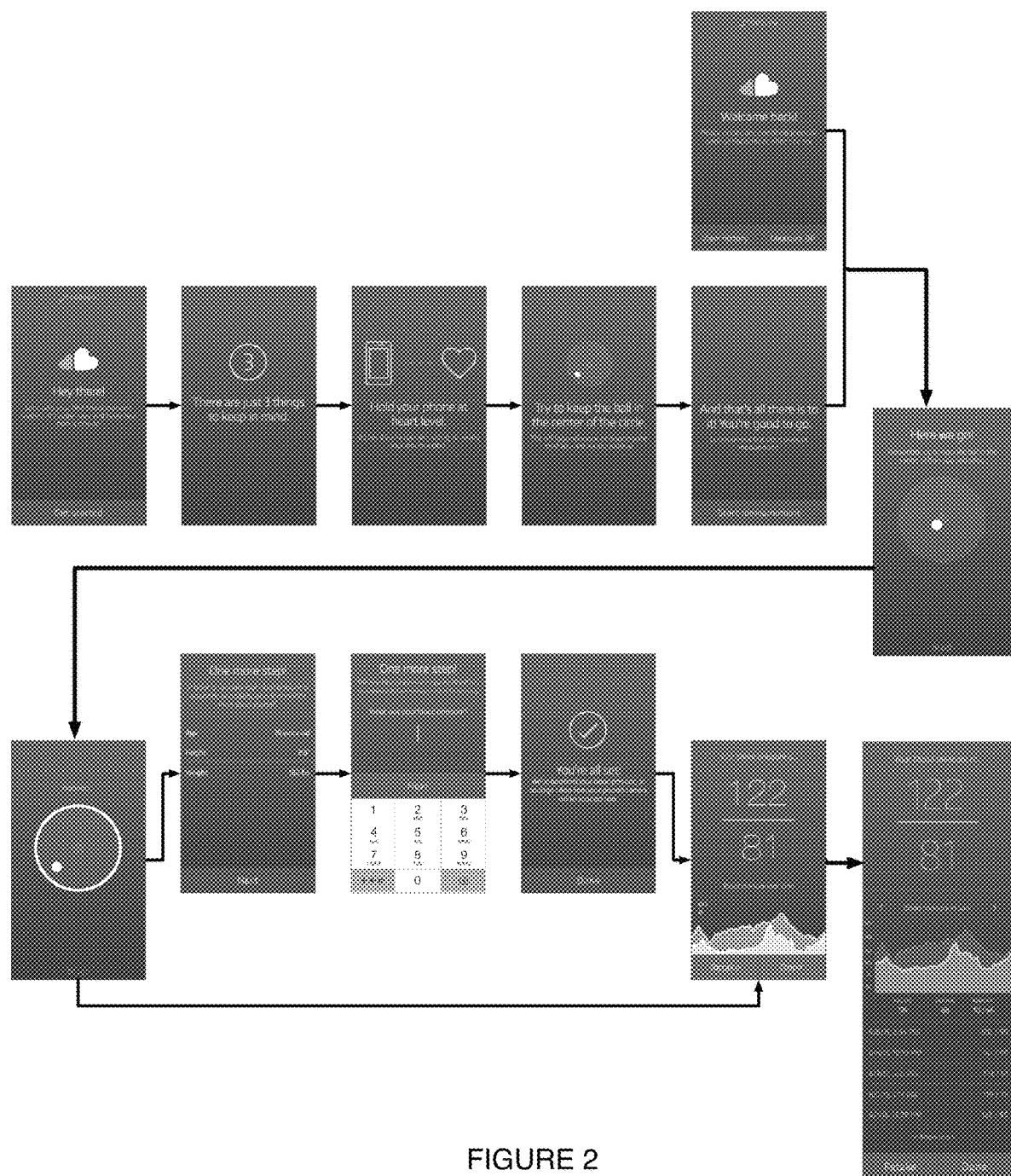
FIG. 2 depicts and example of an application flow used in an embodiment of a method for acquiring data for assessment and management of cardiovascular health.

Block S110 is preferably implemented at a camera module and an illumination module of a mobile computing device of the individual, wherein operational states of the camera module and the illumination module are governed at a native application executing at the mobile computing device of the individual to coordinate generation of the data from the individual. In one such specific example, a native application installed at the mobile computing device of the individual can guide the individual in providing PPG data in coordination with transitioning the camera and illumination modules of the mobile computing device into active states, as shown in FIG. 2 and described in more detail below. Block S110 can additionally or alternatively include transmitting light toward the body region using any other suitable illumination module (e.g., of a non-mobile computing device, of an array of light sources, of a single light source, etc.) in order to acquire data.

Block S110 can include capturing video frame data and/or image data. In variations, video frame data can be captured at frame rates ranging from 20 frames per second to 100 frames per second, and in a specific example, can be captured at 60 frames per second Furthermore, Block S110 can include capturing video/image data in real-time (or near real time), but can alternatively include capturing data in non-real time (e.g., with any suitable delay or lag). Block S110 can include capturing video/image data at a native capture resolution of the camera module (e.g., 1280×720 pixels) or at any other suitable resolution. However, Block S110 can additionally or alternatively be implemented in any other suitable manner.

In relation to processing of data acquired during implementation of Block S110, Block S110 preferably comprises pushing data processing to a graphics processing unit (GPU) of a computing system in communication with or otherwise cooperating with the mobile computing device. Pushing data processing to the GPU thus allows the mobile computing device to maximize potential use of camera module functions of the mobile computing device in relation to limitations in processing capacity at the mobile computing device. The GPU of the computing system can be implemented at a remote server; however, in variations, the computing system can additionally or alternatively comprise personal computer modules, mobile computing device modules, cloud-computing modules, and/or any other suitable computing modules.

Figure 1B:
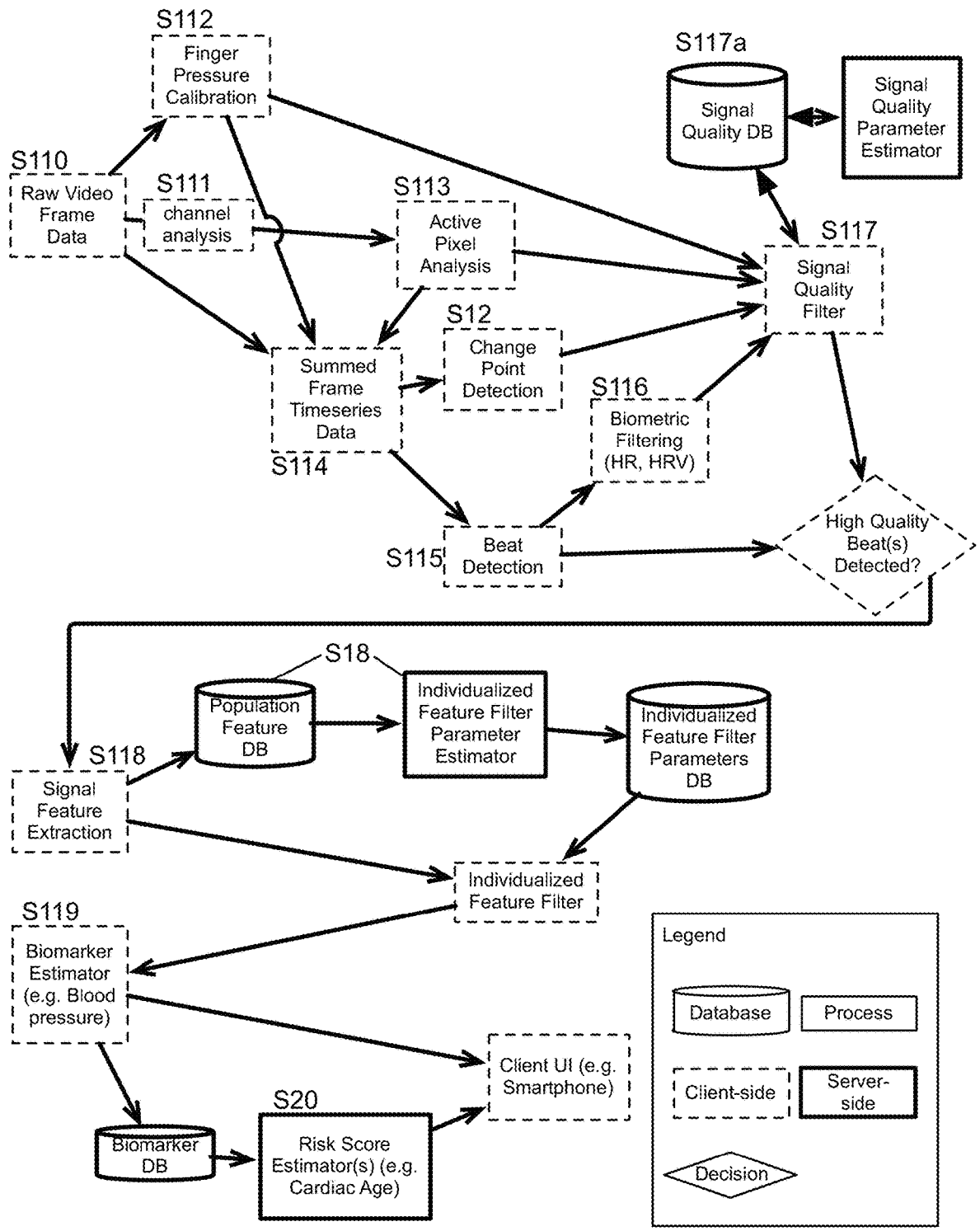
FIG. 1B depicts an embodiment of a method for estimating cardiac biomarkers in near-real time or real time.

As shown in FIG. 1B, in relation to processing, Block S110 can include Block S111, which recites: processing channel data of the time series of data. Block S111 can include processing raw video/image data in Luminance-chroma space (e.g., in relation to YUV color channels). Block S111 can additionally or alternatively include processing raw video/image data in primary-color space (e.g., in relation to RGB color channels). Additionally or alternatively, Block S111 can include processing raw data according to any other suitable image characteristics, embodiments, variations, and examples of which are described in U.S. application Ser. No. 15/183,285 titled "Method and System for Cardiovascular Disease Assessment and Management" and filed on 15 Jun. 2016. Furthermore, Block Sill can include processing channels independently to create filtering and/or estimation parameters per channel; however, Block Sill can alternatively include processing channels together in some manner.

As indicated above, at least some variations of Block S110 can comprise manipulating one or more parameters/operational settings of the hardware components implementing Block S110. In one variation, Block S110 can comprise adjusting a focal length of the camera module (e.g., with manipulation of optical components) of the mobile computing device, and in a specific example, can include minimizing a focal length of the camera module to properly focus on the body region of the individual during the scan of Block S110. Additionally or alternatively, Block S110 can comprise adjusting an acquisition rate of the camera module of the mobile computing device, and in a specific example can include maximizing an acquisition rate (e.g., in terms of frames per second) of the camera module of the mobile computing device. Additionally or alternatively, Block S110 can comprise adjusting a white balance parameter (e.g., tint, temperature) of the camera module of the mobile computing device, and in a specific example can include adjusting a tint of the camera module to maximize green components along a green-magenta tint spectrum. However, Block S110 can additionally or alternatively comprise manipulating any other suitable camera module function of the mobile computing device.

In relation to the camera module used in generating the PPG data from a body region of the individual, Block S110 preferably uses higher resolution camera unit of the mobile computing device to generate scans of the body region, in situations wherein the camera module comprises multiple camera units; however Block S110 can alternatively use any other suitable camera unit of the mobile computing device. In a specific example wherein the mobile computing device comprises an Apple iPhone™ device or other device (e.g., an iPhone 4 S device, an iPhone 5 device, an iPhone 5 S device, an iPhone 6 device, and iPhone 6+ device, an iPhone 6S device, an iPhone 6S+ device, an iPhone 7 device, and iPhone 7+ device, a later model iPhone device, a Samsung™ device, a Nokia™ device, a Google Pixel™ device, etc.), Block S110 can use the back-facing camera unit of the device to scan the body region of the individual; however, in variations of the specific example, Block S110 can alternatively use a front-facing camera unit of the device. Furthermore, while Block S110 preferably implements a built-in camera unit of the mobile computing device, Block S110 can alternatively implement an attachable/removable camera unit coupleable to the mobile computing device in any suitable manner (e.g., with physical coupling, with wireless coupling, etc.).

Furthermore, Block S110 can comprise manipulating illumination functions of the illumination module of the mobile computing device. For instance, Block S110 can comprise manipulating one or more of: an intensity of emitted light, one or more color parameters (e.g., wavelength, etc.) of emitted light, and any other suitable illumination parameter provided by one or more light sources (e.g., light emitting diodes, LEDs; displays, etc.) of the mobile computing device.

In Block S110, the body region of the individual is preferably a finger region of the individual, such that Block S110 can comprise guiding the individual to position a finger region proximal the desired camera unit(s) of the mobile computing device. In a specific example, the individual can thus be guided to hold, pinch, or otherwise contact the appropriate camera unit of the mobile computing device with the desired finger(s) during the scan of Block S110. However, Block S110 can comprise scanning any other suitable peripheral body region of the individual (e.g., upper limb peripheral body region, lower limb peripheral body region). In a specific alternative example, Block S110 can comprise scanning a wrist region of the individual. However, Block S110 can still alternatively comprise generating data from any other suitable non-peripheral body region of the individual.

1.2.1 Method—Calibrating Pressure/Position and Change Point Detection

As shown in FIG. 1B, in relation to the body region interfacing with the camera module, Block S110 can include Block S112, which recites: performing a calibration operation in relation to pressure (e.g., pressure distribution) and position (e.g. positional map) of the body region touching with the camera module, based on image analysis of the time series of data. Block S112 functions to ensure that, during a session of data acquisition, pressure of the body region touching the camera module is factored into calculations of parameters relevant to cardiovascular health of the individual. Block S112 can additionally or alternatively function to normalize and/or correct for session-to-session differences in pressure. Block S112 can include processing pixel-by-pixel intensity variations of the time series of data over time, in order to 1) identify location and 2) pressure of the body region (e.g., finger) touching the camera module.

Block S112 can include processing image gradient features (e.g., gradients in image pixel intensity, gradients in image color channel data, gradients in image luminance channel data, gradients in image chroma channel data, etc.) across pixels of the field of view of the camera module. Block S112 can additionally or alternatively include processing one or more features or gradients over time, across the time series of data, in order to determine one or more of: position of the body region relative to the lens of the camera module, changes in position (e.g., in relation to velocity or acceleration) of the body region relative to the field of view of the camera module, image artifacts associated with undesired objects between the body region and the lens of the camera module (e.g., debris between the finger and the camera lens, smudges on the camera lens, etc.), pressure of each sub-region of the body region touching the camera module, changes in pressure of each sub-region of the body region touching the camera module, and any other suitable position or pressure related/derivative features.

While Block S112 preferably implements image analysis to determine pressure of the body region against the camera module, Block S112 can additionally or alternatively implement one or more of: a pressure sensor, a temperature sensor, a capacitor unit, a force sensor, and/or any other suitable module to determine gross and/or local pressure or position aspects of the body region touching the camera module.

Furthermore, as shown in FIG. 1B, outputs of Block S112 can facilitate Block S12 of the method 100, which recites: detecting changes in at least one of body region position, pressure, and physiology upon calibrating pressure/position of the body region touching the camera module. Block S12 functions to facilitate generation of stable, normalized cardiovascular parameter signatures for accurate biomarker assessment by promoting maintenance of proper positioning and/or pressure of the body region relative to the camera module, and/or by correcting for improper positioning and/or pressure of the body region relative to the camera module.

Block S12 can be implemented after performing the calibration operation of Block S112, or can alternatively be implemented after subsequent portions of the method 100 (e.g., after summation of the time series of data in Block S114). However, Block S12 can additionally or alternatively be implemented at any other suitable point in relation to other Blocks of the method 100, and can additionally or alternatively be implemented multiple times in each iteration of the method 100.

Outputs of Block S112 and S12 can furthermore contribute to downstream portions of the method 100. For instance, outputs of Block S112 can feed into Blocks of the method associated with one or more of: active pixel analysis to determine areas of the frame data that contain pixels that generate high quality waveform signatures associated with cardiovascular activity (e.g., blood pulses); change point detection associated with changes in body region placement, pressure, or physiology; signal quality filtering; signal feature extraction; and any other suitable downstream image processing steps, as described below.

Additionally or alternatively, outputs of Block S112 and/or S12 can be used to guide the individual in repositioning his/her body region relative to the camera module, and/or to guide the individual in applying appropriate pressure (e.g., in a manner that improves signal quality, in a manner that provides consistency with a previous session of scanning, etc.) in manners similar to that described in Section 1.3 of the application. As such, outputs of Block S112 can contribute to user experience/user interface design that implements one or more input modules and output modules of the mobile computing device to guide the individual during a capture session (e.g., within an application executing at the mobile computing device of the individual).

1.2.2 Method—Active Pixel Analysis and Summation of Time Series Data

As shown in FIG. 1B, in relation to processing of the time series of data, Block S110 can include Block S113, which recites: determining regions of each frame of the time series of data containing active pixels, upon performing an active pixel analysis operation on data derived from the time series of image data. Block S113 functions to improve subsequent processing steps by focusing the analysis on regions of interest containing high quality data. Block S113 can include implementing one or more multidimensional scaling techniques, and in specific examples, can include one or more of principal coordinates analysis techniques, Isomap techniques, Torgerson scaling techniques, and any other suitable techniques to determine regions of frames of the time series of data that contain pixels that consistently generate high quality waveform signatures.

Block S113 can additionally or alternatively include any clustering approaches/algorithms for clustering active regions of frames of the times series of data. Block S113 can additionally or alternatively include refining estimations or determinations of active pixel regions by using population data and/or individual data of body regions scanned in previous sessions.

As shown in FIG. 1B, in relation to processing of the time series of data, Block S100 can include Block S114, which recites: summing the time series of data using reduction operations to produce a summed time series of data, which functions to aggregate data and facilitate performance of normalization operations for determination of one or more parameters relevant to cardiovascular health of the individual. Block S114 can include parallel reduction operations (e.g., in relation to GPU-based data processing), where active pixel region determinations from Block S113 and/or position and pressure calibration data from Blocks S112 and S12 can be used to normalize the summed time series of data for fine body region positioning and/or pressure changes during a capture session.

1.2.3 Method—Beat Detection and Biometric Filtering

As shown in FIG. 1B, Block S100 can include Block S115, which recites: determining data portions associated with sequences of full cardiac cycle events upon processing the summed time series of data. Block S115 functions to identify an onset and/or termination point of each beat represented in the time series of data, in order to extract parameters relevant to monitoring cardiovascular health of the individual(s) in subsequent portions of the method 100. Block S115 can, for a segment of the time series of data, include 1) setting an onset marker (e.g., a time point marker) for a cardiac cycle; 2) identifying if a full cardiac cycle has occurred based upon beat signatures associated with a cardiac cycle; and if a full cardiac cycle has occurred, 2) re-setting the onset marker to the time point at which the cardiac cycle has ended (e.g., a "current" time point). Thus, the time points of each portion of each cardiac cycle represented in the time series of data can be determined in Block S115, in order to estimate parameters relevant to cardiovascular health in subsequent blocks of the method 100.

Determining if a complete cardiac cycle has occurred can be based upon identification of complete beat complexes (e.g., QRS complexes, etc.) represented in a segment of the time series of data in any suitable manner; however, Block S115 can additionally or alternatively include implementation of embodiments, variations, and/or examples of methods described in U.S. application Ser. No. 15/183,285 titled "Method and System for Cardiovascular Disease Assessment and Management" and filed on 15 Jun. 2016.

As shown in FIG. 1B, Block S110 can further include Block S116, which recites: performing a biometric filtering operation on the sequence of full cardiac cycle events of Block S115, which functions to determine one or more heart beat-derived parameters from the sequence of full cardiac cycle events. Block S116 preferably includes determining heart rate (e.g., number of beats per unit time) and heart rate variability (e.g., variations in time intervals between beats). Block S116 can additionally or alternatively include determining any other suitable heart beat-derived parameters for the individual. Furthermore, one or more parameters determined using the biometric filtering operation of Block S110 can be filtered using physiologically relevant thresholds. As such, in a first example, Block S116 can include omitting or correcting one or more heart rate values determined, if the heart rate value determined is outside of a threshold range of physiologically-relevant values. In a second example, Block S116 can include omitting or correcting one or more heart rate variability values determined, if the heart rate variability value determined is outside of a threshold range of physiologically-relevant values. However, Block S116 can additionally or alternatively implement any other suitable physiologically-relevant threshold for filtering biometric parameters (e.g., heart rate, heart rate variability, etc.) determined in Block S116.

1.2.4 Method—Signal Quality Filtering, Storage, and Parameter Estimation

As shown in FIG. 1B, Block S110 can additionally include Block S117, which recites: performing a signal quality filtering operation on the series of time data and outputs of the calibration operation of Block S112, the active pixel analysis operation of Block S113, the change detection operation of Block S12, and the biometric filtering operation of Block S116. Block S117 functions to determine a signal quality assessment heuristic that retains high quality data for further downstream processing, and removes data associated with below-threshold signal quality. Block S117 is preferably implemented in real time or near-real time, such that the signal quality associated with each current window is assessed as the data is received and, if the signal quality surpasses a threshold signal quality condition, the data associated with the current window is passed to subsequent blocks of the method for further processing to extract relevant features of interest and/or to estimate values of parameters relevant to cardiovascular health.

In Block S117, the threshold signal quality condition can be aggregated from one or more of: a calibration metric of Block S112 (e.g., a pressure-related metric, a position-related metric); a change metric of Block S12 (e.g., a metric associated with pressure variability across the time series of data, a metric associated with position variability across the time series of data, a metric associated with physiological change across the time series of data, etc.); a metric associated with the active pixels determined in Block S113 (e.g., a ratio of active to inactive pixels across frames of the time series of data; a number of active pixels within a frame of the time series of data, a variability metric associated with active pixels across frames of the time series of data, etc.); and a metric associated with outputs of the biometric filtering operation (e.g. heart rate metric, confidence in the heart rate metric based on physiological thresholds, confidence in the heart rate variability metric based on physiological thresholds, percent of the time series of data associated with biometric parameter values outside of physiological thresholds, etc.).

In relation to the signal quality filtering operation of Block S117, Block S117 can include transmitting signal quality data of the time series of data for all capture sessions associated with all individuals to one or more databases (e.g., remote servers, etc.) S117a. As such, aggregated signal quality data can be stored and retrieved for future use (e.g., in relation to refinement of signal quality parameter determinations, in relation to refinement of algorithms for signal quality determination and/or downstream processing of data). In such variations, signal quality parameters generated from capture sessions of a population of individuals can be used to refine signal quality heuristic algorithms for increasing sensitivity and specificity of signal quality in future sessions of capturing time series of data from individuals.

1.2.5 Method—Population Features and Individualized Features

As shown in FIG. 1B, Block S110 can additionally include Block S118, which recites: performing a signal feature extraction operation upon outputs of Block S115, S116, and S117, in relation to detected cardiac cycles and data portions where signal quality satisfies threshold conditions. Features can be extracted using one or more feature extraction techniques in relation to processing waveform signatures (e.g., zero crossings, inflection points, peaks, valleys, sub-waveform shapes, waveform derivative features, waveform integrated features, etc.). In specific examples, feature extraction in Block S118 can include extraction of features from first/second/higher order-derivative zero-crossing techniques, direct cosine transformation techniques, other techniques for extracting characteristic signals from waveforms, and any other suitable technique for feature extraction.

In relation to Block S118, individualized feature parameter estimation can comprise implementing probability density functions for the individual and/or the population of individuals as asynchronous processes, where individual parameter limits can be re-determined iteratively using linear or non-linear machine learning techniques, some of which are described below. In a manner similar to Block S117a, Block S118 can include transmission of individualized feature parameters to one or more databases for retrieval and further processing.

While some examples of signal feature processing and extraction methods are described above, Block S118 can implement any other suitable feature extraction methods, embodiments, variations, and examples of which are described below and in U.S. application Ser. No. 15/183,285 titled "Method and System for Cardiovascular Disease Assessment and Management" and filed on 15 Jun. 2016. In relation to performing the signal feature extraction operation, Block S118 can include Block S118a, which recites transmitting signal features extracted using the signal feature extraction operation to a database for storage and further processing, in relation to feature analysis across the population of individuals.

As shown in FIG. 1B, once individual features are extracted the method 100 can include Block S18, which recites: performing a feature filtering operation upon outputs of the signal feature extraction operation of Block S118. Block S18 functions to compare extracted features of Block S118 to determined feature threshold conditions for the individual (and/or the population of individuals), in terms of one or more specific metric limits.

In Block S18, the feature condition can be associated with one or more waveform feature metrics including one or more of: a peak amplitude, a valley amplitude, characteristics of a foot region of a waveform, characteristics of an onset region of a waveform, characteristics of a termination region of a waveform, characteristics of an intermediate region of a waveform, characteristics of a zero crossing of a waveform, characteristics of a slope (or other derivative metric) of a waveform, characteristics of an integrated portion of a waveform, characteristics of similarity across different waveforms associated with different cardiac cycles (e.g., in relation to similarity metrics), trends across waveforms (e.g., in relation to waveform drift due to sensors or other aspects), and any other suitable metrics. If outputs of Block S18 indicate that parameters are within limits, such signal features can be passed to subsequent blocks of the method 100 for estimation of biomarkers relevant to cardiovascular health.

1.2.5.1 Method—One Feature Selection Workflow for Signal Feature Extraction

In one such variation of Blocks S115, S116, S117, and S118, the method 100 can include representative Block S160, which recites: within the time series of image data, identifying a reference window of time for extracting features across the time series of image data, wherein the features extracted are relevant to assessment of CVD of the individual. Block S160 functions to facilitate subsequent processing of the time series of image data in order to extract parameters relevant to assessment/monitoring of CVD in the individual. Block S160 can additionally function to identify windows of time associated with poor signal quality, in relation to windows associated with higher signal quality. In one variation, Block S160 can comprise segmenting the signal derived from the time series of image data into smaller windows of time, and processing the signals associated with the windows of time against each other in order to identify the best window of time to use as a reference window for other windows. Furthermore, in some variations, the window size can be varied in the reference window selection process. Block S160 can be performed in near real time, or can alternatively be performed in non-real time (e.g., during post processing of data).

Figure 5:
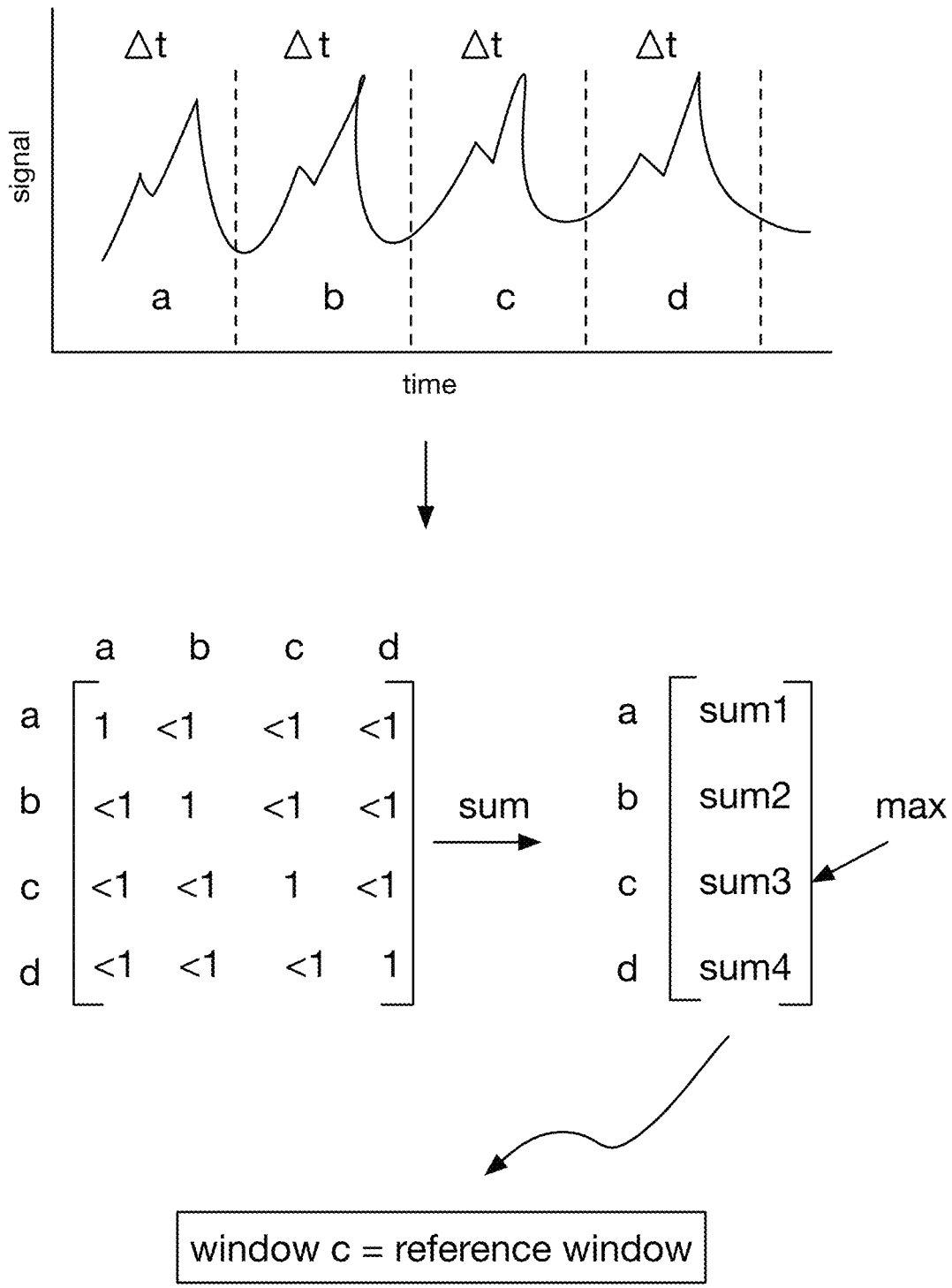
FIG. 5 depicts an example of a portion of a method for acquiring data for assessment and management of cardiovascular health.

In a specific example, Block S160 comprises segmenting the signal derived from the time series of image data into 3 second windows of time, and implementing a combinatorial search algorithm to identify the "best" 3 second window of time for use as a reference window. In more detail, as shown in FIG. 5, the signal associated with each window can be correlated against signals associated with other windows in a cross-correlation process, with the correlation coefficients organized in matrix form (e.g., 2×2 matrix form). The correlation coefficients for each window can then be summed (e.g., across rows of the matrix, across columns of the matrix, etc.), and identification of the highest sum can be used to identify the reference window that has the highest correlation with other windows. However, the reference window of time can be determined in any other suitable manner and/or have any other suitable size.

For instance, in alternative variations, Block S160 can comprise processing in the time domain and/or the frequency domain, to identify any other suitable reference (e.g., reference peak, as opposed to reference window) with steps including one or more of: another suitable segmentation process (e.g., multi-stage bandpass filters with nearest-neighbor decision logic and interbeat-interval limitations, repeated Gaussian filters, etc.); a non-segmentation process (e.g., with an adaptive frequency estimator, with a Kalman filter, etc.); identification of primary and/or secondary peaks with a rising slope analysis (e.g., involving determination of derivatives in the signal); implementation of scaling functions across signals associated with different windows of time (e.g., in relation to beat variability); performance of any other suitable cross-correlation function; and performance of any other suitable process to identify the reference(s).

In some variations, the method 100 can additionally or alternatively include extracting a set of reference windows that are characteristic of different subpopulations of individuals, upon processing reference windows of time series image data from a population of individuals in association with a set of characterizations of the population of individuals S165, which can function to generate "biomarkers" that can be used to diagnose, characterize, or facilitate data processing for different populations or/subpopulations of individuals. For instance, by analyzing the reference window(s) for each individual of a population of individuals, in association with characteristics (e.g., demographic information, comorbidity information) of the individuals, features of the reference windows can be used as diagnostic tools/characterization tools for different subpopulations of individuals.

In relation to use of the reference windows as biomarkers, Block S165 can comprise a clustering process (e.g., unsupervised clustering, supervised clustering) of the reference windows in relation to different demographic and medical characteristics of the individuals, to determine predictive capacity of the reference windows. Additionally or alternatively, Block S160 can implement a correlation process that correlates features of the reference windows with one or more characteristics of the individuals. Additionally or alternatively, Block S160 can implement a machine learning algorithm that is trained with a training dataset (e.g., training data acquired from another measurement device). In variations, the machine learning algorithm can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

In one example, Block S165 can comprise determining reference windows of PPG data for each of a population of individuals, wherein the individuals are organized by age (e.g., in a first age group from 18-35 years old, in a second age group from 36-64 years old, in a third age group of over 65 years old), gender (e.g., 50/50 male/female), and disease state (e.g., 40% with pre-existing cardiovascular disease conditions (e.g., HTN). However, in variations, the population of individuals can additionally or alternatively be organized based upon one of more of: ethnicity, sexual orientation, family history, medical history, family size, marital status, height, weight, and any other suitable characteristic. In the specific example, each individual can be prompted to take two sittings of three coordinated measurements (e.g., with both the PPG mobile-device method described above and a blood pressure cuff method) spaced apart by five minutes, wherein each sitting is spaced apart by 30 minutes. Finally, in the specific example, identified reference windows can be processed with a clustering process (e.g., unsupervised clustering, supervised clustering) in relation to different demographic and medical characteristics of the individuals, to determine predictive capacity of the reference windows. However, variations of the specific example of Block S165 can alternatively be implemented in any other suitable manner.

1.2.6 Method—Biomarker Determination

As shown in FIG. 1B, Block S110 can additionally include Block S119, which recites: performing a biomarker estimation operation upon outputs of the feature filtering operation of Block S118, which functions to transform signal features into one or more interpretable biomarker parameters associated with cardiovascular health. Block S119 can thus include transforming outputs of the feature filtering operation into one or more of: an estimated value of blood pressure (e.g., instantaneous blood pressure, average blood pressure, etc.); blood pressure variation (e.g., diurnal blood pressure variation); an arterial stiffness index; a parameter indicative of phase of constriction; a pulse transit time; a pulse wave velocity, and/or any other suitable cardiovascular biomarker types. Cardiovascular biomarkers values can indicate hypertension, atherosclerosis, narrow of blood vessels, arterial damage, and/or any other cardiovascular risk factor, as described in U.S. application Ser. No. 15/183,285 titled "Method and System for Cardiovascular Disease Assessment and Management" and filed on 15 Jun. 2016.

In implementation, Block S119 can include processing signal features that pass threshold conditions using estimation functions (e.g., non-linear functions that process the signal features) of applications executing at the mobile computing device(s) of the individual(s). However, Block S119 can additionally or alternatively include implementing any other suitable functions, and/or processing at any other suitable computing component of the system(s) described (e.g., non-mobile device computing subsystems). Furthermore, similar to other Blocks of the method 100, Block S119 can include transmitting determined biomarker values of Block S119 to one or more suitable databases for storage and further analyses (e.g. in relation to refinement of algorithms for biomarker determination). In some variations, stored biomarkers can be used in asynchronous parameter estimation routines to refine one or more of: population estimators of biomarker parameter values and individual estimators of biomarker parameter values. However, stored values can additionally or alternatively be processed subsequently in any other suitable manner.

1.2.7 Method—Risk Score Estimation

As shown in FIG. 1B, Block S110 can additionally include Block S20, which recites: determining a cardiovascular health risk score from outputs of the biomarker estimation operation of Block S119, which functions to assess severity of a current, past and/or future cardiovascular health state of an individual or population of individuals based upon comparison of one or more biomarker parameter values to threshold condition values. Block S20, can include generating comparisons between different biomarker parameter values and respective threshold conditions, and based upon the comparisons, generating analyses indicative or diagnostic of one or more of: stress, cardiac age, sleep quality, rest quality, cardiovascular health, risk of being diagnosed with one or more cardiovascular diseases, and/or any other suitable analysis associated with health risks. In one specific example, a combination of an above threshold resting heart rate, an above threshold heart rate variability, an above threshold night time blood pressure, and a high degree of arterial stiffness can be used in Block S20 to output a risk score indicative of an "older-than-expected" cardiac age and diagnostic of cardiovascular disease (e.g., in relation to heart attack risk, in relation to stroke risk, etc.). However, Block S20 can be implemented in any other suitable manner.

Outputs of one or more of Blocks S111-S119 and S12, S18, and S20 can be provided to parties of interest (e.g., third-party clients, the individual, an entity associated with the individual, etc.) immediately after acquisition or determination, and/or asynchronously based upon one or more factors (e.g., shifts in parameter values, shifts in risk scores, shifts in risk score stratification across a population of individuals, etc.), in manners similar to that described in Section 1.4 below. Furthermore, one or more outputs of Blocks S110-S119 and S12, S18, and S20 can be used to automatically provide therapeutic interventions to the individual(s). Automatically providing therapeutic interventions to the individual(s) can include one or more of: automatically modulating medication provision, automatically adjusting an environmental aspect of the user, providing a medical recommendation, facilitating telemedicine digital communications between a user and another entity, and/or any suitable therapy approach. Therapy provision is preferably partially or fully implanted at a remote server (e.g., a remote server implementing other Blocks of the method, but can be implemented at any suitable component). In variations, automatically providing therapeutic interventions can include transmitting instructions to a mobile computing device, the instructions prompting the mobile computing device to instruct a secondary mobile computing device to apply the therapy. In a specific example, intervention provision can include generating, at a remote server, instructions for automatically adjusting an environmental aspect of the user; transmitting the instructions to a mobile computing device (e.g., a smartphone connected to a home network of the user) the instructions prompting the mobile computing device to wirelessly communicate with a secondary device to adjust the environmental aspect (e.g., a television connected to the home network of the user). However, automatically facilitating therapy provision can be performed in any suitable manner.

In a first variation automatically providing therapeutic interventions can include automatically modulating medication provision. Characteristics of medication provision that can be modulated include: dosage level, dosage frequency, type of medication, medication regimen, medication information, prescription renewal, prescription retrieval, and/or any other suitable medication provision characteristic. Modulation of medication provision can include providing notifications regarding the modulation (e.g., providing a notification to take a blood pressure medication based on a characterized diurnal blood pressure variation as in Block S260 and/or Block S270), automatically communicating with another entity (e.g., renewing a prescription with a pharmacy, contacting a care provider regarding the medication, etc.), and/or any suitable action. Automatically facilitating therapy provision can be implemented using automatic medication dispensing apparatus (e.g., a wirelessly-connected medication dispenser), such that this variation of intervention provision include providing commands from the computing system to the medication dispenser based upon analyses outputted from previous blocks of the method 100. However, automatically modulating medication provision can be performed in any suitable manner.

Additionally or alternatively, in a second variation, automatically providing therapeutic interventions include automatically adjusting an environmental aspect of the user. Adjusting an environmental aspect can include: selecting an environmental aspect to adjust from at least one of lighting audio, and temperature; determining a degree of adjustment (e.g., how much lighting, audio, or temperature to adjust), a timing of adjustment (e.g., automatically adjusting in response to generating an analysis of a cardiovascular parameter, scheduling an adjustment for a particular time or frequency, etc.), and/or any suitable characteristic. A lighting environmental aspect can be the lighting of a mobile computing device of the user (e.g., the mobile computing device used in capturing the time series of image data from which a cardiovascular parameter is determined), a connected lightbulb (e.g., a smart lightbulb connected on the same network as a smartphone of a user), and/or any other suitable lighting component. An audio environmental aspect can be an audio of a mobile computing device (e.g., automatically controlling a mobile computing device to play a selected audio tone or musical sample, modifying the volume setting of a mobile computing device, etc.), a connected audio output device (e.g., a speaker, a television, a secondary mobile computing device, etc.), and/or any suitable device. A temperature environmental aspect can be controlled through a temperature control device (e.g., a connected thermometer, a connected air conditioning and/or heating system, etc.). However, environmental aspects can possess any suitable characteristic, and adjusting an environmental aspect can be performed in any suitable manner.

Additionally or alternatively, in a third variation, automatically providing therapeutic interventions can include providing a medical recommendation. A medical recommendation can be provided to one or more of: a user (e.g., for the user to implement themselves), a care provider, a guardian, and/or any suitable entity. A medical recommendation can include a recommendation to perform a specific action (e.g., to take a walk, to rest, to think positive thoughts, etc.), to stop performing a specific action, to take a medication, to communicate with other entity, and/or any suitable activity. The medical recommendation is preferably provided at the mobile computing device associated with the entity to be notified, but can be provided at any suitable device.

Additionally or alternatively, in a fourth variation, automatically providing therapeutic interventions can include facilitating a digital communication between a user and another entity. A digital communication is preferably enabled between a user and a care provider, but can be enabled between a user and a guardian and/or any relevant entity. A digital communication is preferably enabled through an application (e.g., a phone calling application, a text messaging application, an application implementing portions of the method 100, etc.), executing on a mobile computing device associated with a user, but such digital communication can be facilitated through any suitable venue. Facilitating a digital communication between a user and another entity can include: providing an analysis of a cardiovascular parameter to one or more of the user and the other entity, guiding the user and/or the other entity through review of the analysis and/or generation of a treatment based on the analysis, and/or any suitable action. However, automatically facilitating therapy provision can be performed in any other suitable manner.

1.2.8 Method—Other Hardware Manipulation Aspects

Any one or more blocks of the method 100 described below can additionally or alternatively be used for signal quality determination and/or cardiovascular health parameter determination:

Block S140 recites: normalizing the time series of image data upon reception of an environmental dataset generated using a supplementary sensor module of the mobile computing device. Block S140 functions to generate data that can be used to normalize the time series of image data, using sensors of the mobile computing device that can provide contextual data. In one variation, Block S140 comprises using a camera module of the mobile computing device to acquire ambient light data from the environment of the individual, while the body region of the individual is being scanned in Block S110, such that the ambient light data can be used to correct or normalize the PPG data of Block S110 in relation to the environment of the individual. In variations, normalization can comprise one or more of: applying a transform to the data of Block S110 based upon the spectral characteristics of ambient light in the environment of the individual; removing ambient light components from the data of Block S110; and processing the data of Block S110 with the data of Block S140 in any other suitable manner.

In relation to the camera module used to receive ambient light data in Block S140, Block S140 preferably uses lower resolution camera unit of the mobile computing device to generate the ambient light data, in situations wherein the camera module comprises multiple camera units; however Block S140 can alternatively use any other suitable camera unit of the mobile computing device. In a specific example wherein the mobile computing device comprises an Apple iPhone™ device or other device (e.g., an iPhone 4S device, an iPhone 5 device, an iPhone 5S device, an iPhone 6 device, and iPhone 6+ device, an iPhone 6S device, an iPhone 6S+ device, an iPhone 7 device, and iPhone 7+ device, a later model iPhone device, a Samsung™ device, a Nokia™ device, a Google Pixel™ device, etc.), Block S140 can use the front-facing camera unit of the device to acquire ambient light data; however, in variations of the specific example, Block S140 can alternatively use a back-facing camera unit of the device.

Furthermore, while Block S140 preferably implements a built-in camera unit of the mobile computing device, Block S140 can alternatively implement an attachable/removable camera unit coupleable to the mobile computing device in any suitable manner (e.g., with physical coupling, with wireless coupling, etc.). Additionally or alternatively, Block S140 (and/or Block S110) can implement any other suitable light sensor (e.g., optical spectrometer), can implement multiple light sensors/cameras for holistic acquisition of ambient light conditions (e.g., with light sensors placed at multiple positions within the environment of the individual), and/or can implement any other suitable system configuration for data acquisition.

Still alternatively, Block S140 can be supplemented or substituted with methods for controlling ambient light in the environment of the individual. For instance, in controlling environmental light effects, the individual can be guided to provide PPG data in a dark environment (e.g., in a room with the lights shut off, with the mobile computing device and the body region of the individual covered), such that the illumination used to generate the PPG data is controlled (e.g., by the illumination module of the mobile computing device). Block S140 can, however, be implemented in any other suitable manner.

Block S150 recites: with at least one sensor module of the mobile computing device, generating a supplementary dataset indicative of at least one physiological state of the individual. In at least one variation, Block S150 functions to facilitate identification of at least one physiological state of the individual that could be detrimental to generation of suitable data in Block S110. Additionally or alternatively, in variations, Block S150 can function to use one or more sensor modules of the mobile computing device to supplement the image data generated in Block S110, in relation to enriching CVD-related diagnostics of the individual.

Figure 3:
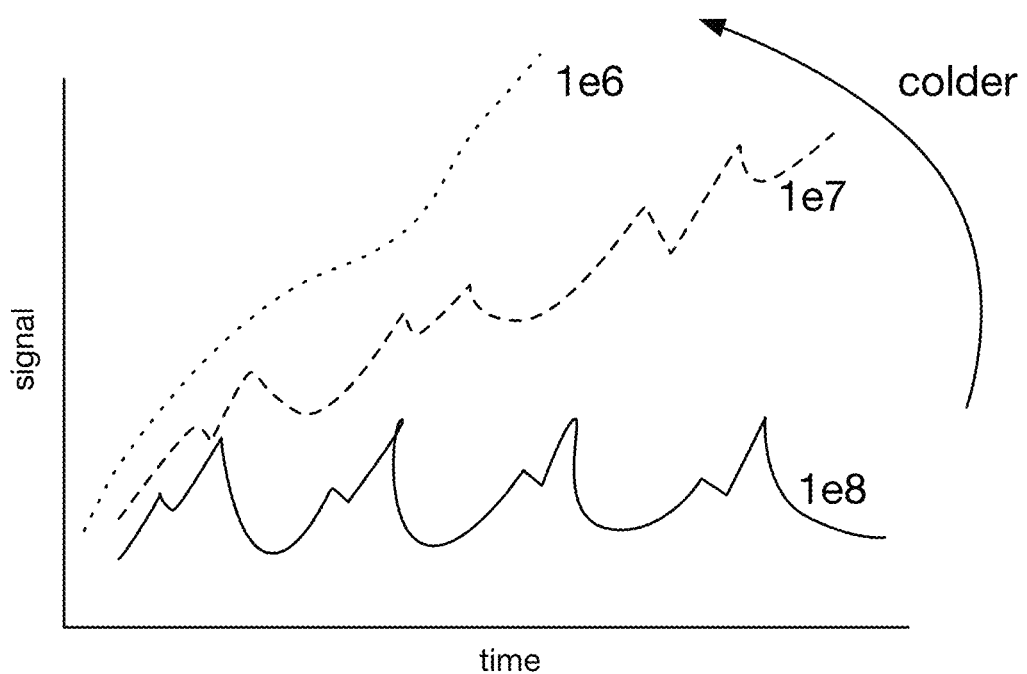
FIG. 3 depicts an example of detection of physiological states that could contribute to poor signal quality in an embodiment of a method for acquiring data for assessment and management of cardiovascular health.

In a first set of variations, Block S150 can include steps that enable identification of at least one physiological state of the individual that could be detrimental to generation of suitable data in Block S110. In one variation, Block S150 can comprise identifying a body region temperature state of the individual, wherein a detected body region temperature below a temperature threshold can be detrimental to signal acquisition in Block S110. For instance, in relation to the body region being a fingertip, if the individual's fingertip is colder than a specific temperature threshold, localized heating resulting from an illumination module (e.g., LED heating) can produce physiological perfusion (i.e., flushing) of the fingertip region of the individual, which can in turn produce signal noise. In an example shown in FIG. 3, signal noise caused by body temperature at the site of interrogation can contribute to unsuitable data generation, which can be used to inform the types of information output in Block S170 of the method 100. For instance, upon detection that the body region of the individual has an unsuitably low temperature, Block S150 can be used to inform the individual that his/her body region temperature is too low for suitable signal generation, and/or Block S150 can be used to guide the individual in performing behaviors that will restore his/her body region temperature to a suitable temperature state.

Additionally or alternatively, aggregation of such data (e.g., longitudinally across time, over a population of individuals) can be used to generate or otherwise determine proxies for other CVD-related conditions (e.g., peripheral vascular disease), wherein characteristics of changes in perfusion can be tracked over time/across a population of individuals to characterize changes in blood flow to peripheral body regions of individuals.

In related variations, additional sensors (e.g., of the mobile computing device, of biometric monitoring devices worn by the individual, etc.) can be used in Block S150 to facilitate identification of at least one physiological state of the individual that could be detrimental to generation of suitable data in Block S110. For instance, a microphone (e.g., of the mobile computing device of the individual) can be used to generate acoustic signals (e.g., resulting from the individual's heart beating, etc.) that can be processed to determine if a physiological state of the individual would be non-conducive to generation of suitable signals in Block S110. Additionally or alternatively, a proximity sensor can be used to determine if the body region of the individual is at a suitable distance from the camera module implemented in Block S110 for signal generation. Additionally or alternatively, any sensors of one or more biometric monitoring devices worn or otherwise coupled to the individual can be used to generate biometric data indicative of anticipated signal quality.

In a second set of variations, Block S150 can include steps for generation of additional data that supplements the image data generated in Block S110, in relation to enriching CVD-related diagnostics of the individual. For instance, in one variation, Block S150 can comprise implementing a force sensor of the mobile computing device (e.g., a force sensor in communication with the display of the mobile computing device) to unobtrusively generate ballistocardiography data derived from forces resulting from the individual's heart beating (e.g., from a force-sensing touch system of the mobile computing device). In examples, force data can facilitate detection of bruits and/or other anomalies (e.g., arrhythmias, stiff blood vessels) detectable within force data. In one specific example, a force sensor module (e.g., 3D touch module, force touch module, etc.) of an Apple™ device (e.g., an iPhone 4S device, an iPhone 5 device, an iPhone 5S device, an iPhone 6 device, and iPhone 6+ device, an iPhone 6S device, an iPhone 6S+ device, an Apple Watch, etc.) or other device can be used to generate force data resulting from perfusion, which can be used to detect perfusion forces over time and/or indirectly measure blood vessel stiffness parameters from the body region of the individual.

Additionally or alternatively, Block S150 can comprise generation of acoustic data, using a microphone of the mobile computing device, from a heart region of the individual. The acoustic data can thus be used, according to the method 100, to acoustically detect one or more parameters characterizing the heart beat of the individual, to supplement the image data received in Block S110. Additionally or alternatively, a magnetometer (or comparable sensor) of the mobile computing device can be used to generate electrocardiogram (ECG) data from the cardiovascular system of the individual. As such, the sensor(s) of the mobile computing device can provide a comprehensive dataset from which features associated with CVD/HTN can be extracted. For instance, data acquired over time in Blocks S110, S140, and/or S150 can be used to assess one or more of: changes in edema, changes in stroke volume/perfusion strength of the heart of the individual as an indication of future heart failure (e.g., based upon Starling's law), and any other suitable cardiography-related or derived parameter.

While the method blocks above describe implementation of sensors of a mobile computing device, variations of the method 100 can additionally or alternatively implement sensors of any other suitable device(s) that can detect changes in physiology/function of the cardiovascular system of the individual. For instance, one or more non-mobile device components (e.g., of a wearable computing device, of sensors configured in the environment of the individual, of sensor modules coupleable to the mobile computing device, etc.) can substitute or supplement the sensor modules described in examples and variations above.

1.3 Method—User Experience/User Interface Control

Block S120 recites: in cooperation with receiving at least a portion of the time series of image data, directing the individual to vary a configuration of the mobile computing device according to a set of orientations in space. Block S120 functions to facilitate identification of at least one configuration of interaction between the individual and the mobile computing device that produces a signal of desired quality. As such, one or more outputs of Block S120 can additionally or alternatively contribute to signal quality operations, signal feature determination operations, biomarker estimation operations, and/or any other suitable operations described in relation to Blocks S110-S119 and S12, S18, and S20 above. Block S120 preferably comprises guiding the individual (e.g., within a native application executing at the mobile computing device) to vary the orientation of the mobile computing device in space while a signal (i.e., portion of the time series of image data) is being acquired from the body region of the individual, and assessing the quality of the signal in each of the set of orientations in order to determine at least one orientation associated with a signal of desired quality.

Figure 4:
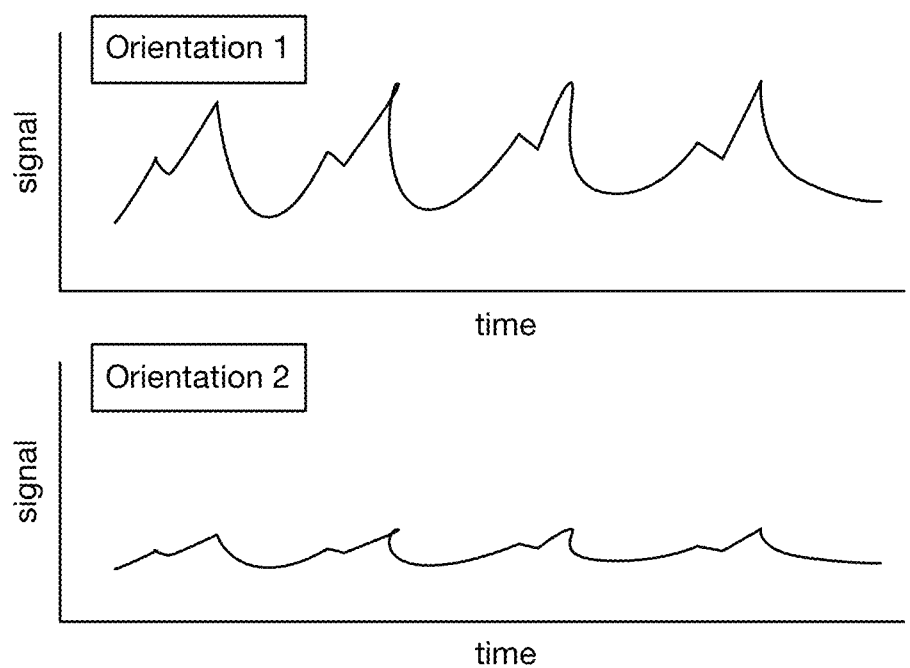
FIG. 4 depicts an example of orientation-specific signal effects in an embodiment of a method for acquiring data for assessment and management of cardiovascular health.

In Block S120, the set of orientations in space can be a predetermined set of orientations, such that the individual is guided to sequentially vary the orientation of the mobile computing device according to the configuration of each of the predetermined set of orientations; however, the set of orientations can alternatively not be predetermined, such that the individual is able to freely adjust the orientation of the mobile computing device in space. Preferably, each of the set of orientations has a specific definition, wherein the definition comprises one or more of: a position within a 2D or 3D coordinate system (e.g., Cartesian coordinates, polar coordinates, cylindrical coordinates, etc.) and rotation about any suitable number of axes. In a specific example, the configuration of each orientation is defined as a function, $f(\phi, \psi, \theta, t)$, wherein $\phi$, $\psi$, and $\theta$ are axes of rotation and t is time, and the different orientations produce different signal amplitudes, as shown in FIG. 4. However, any other suitable definition can be used. Preferably each orientation is detectable using one or more internal motion detection modules (e.g., accelerometer, gyroscope, etc.) of the mobile computing device; however, the orientation(s) can be detected in any other suitable manner (e.g., with a module external to the mobile computing device).

As shown in the example of FIG. 2, the individual may or may not be aware of the process of Block S120, such that the individual is prompted to vary the orientation of the mobile computing device in a gamified manner within an application executing at the mobile computing device. However, any other suitable graphic(s) may be rendered in guiding the individual to vary the orientation of the mobile computing device in a desired manner.

Block S130 recites: based upon the portion of the time series of image data associated with the set of orientations, identifying an orientation of the set of orientations that produces a signal of desired quality, and prompting the individual to maintain the orientation during generation of the time series of image data. In combination with Block S120, Block S130 functions to facilitate consistent generation of high quality PPG data from the individual, based upon mobile computing device orientation-dependent variations in signal quality. Furthermore, Block S130 can function to reinforce behaviors of the individual that contribute to good signal quality, in combination with the outputs of Block S110.

In identifying the orientation(s) that produce(s) good signal quality, Block S130 can comprise one or more of: identifying one or more features (e.g., peaks, signal-to-noise ratio, peak amplitude, trough, trough amplitude, trough depth difference, Euclidean distance, etc.) of the signal stream associated with the time series of image data; processing the feature(s) to determine a derivative metric associated with signal quality (e.g., average peak amplitude, etc.); and selecting the orientation associated with the value of the derivative metric that produces the most preferable signal quality. As such, implementation of Block S130 can identify the orientation of the mobile computing device that provides the highest degree of discernment between features of the signal associated with the time series of image data.

In relation to the variations described above, for each orientation of the mobile computing device and over a window of time, Block S130 can implement a peak detection algorithm (e.g., associated with amplitudes of portions of the time series of image data) that identifies peaks (e.g., peaks in value of one or more light-derived features of the image data), wherein the peak detection algorithm can operate with any suitable fitting and/or smoothing function to identify the signal peaks. Once the peaks are identified, Block S130 can include determining an average peak amplitude from the identified peaks. Finally, the average peak amplitude can be used to select the "best" orientation, wherein the best orientation for data acquisition is characterized by the highest average peak amplitude across all orientations of the mobile computing device. However, variations of Block S130 can include any other suitable alternative step(s) for selecting the orientation of the mobile computing device that results in desired data quality.

In a specific example, as shown in FIG. 2, outputs of Blocks S120 and S130 can be used to guide the individual, within an application, to maintain the orientation of the mobile computing device that results in the best signal quality. In more detail, the application can guide the individual to keep a rendered ball graphic at a central region of a rendered circle graphic, wherein the position of the ball graphic relative to the circle graphic changes as the individual varies the orientation of the mobile computing device. However, any other suitable feedback (e.g., audio feedback, haptic feedback, visual feedback, etc.) can be used to prompt the individual to maintain the desired orientation of the mobile computing device during a scan. Furthermore, the individual can be guided to perform any other suitable behavior conducive to improving signal quality (e.g., holding the mobile computing device/scanning device at heart level, etc.), as shown in FIG. 2.

1.4 Method—Signal Quality Assessment and Information Output

Block S110 recites: based upon one or more of the outputs of Blocks S110 through S160, informing at least one of the individual and an entity upon detection that an unsuitable signal associated with the time series of image data has been obtained. Block S110 can additionally or alternatively include outputting relevant CVD-associated metrics for informing the individual or an entity associated with the individual. Block S110 functions to apply the analyses of one or more of Blocks S110-S165, in order to indicate to the individual (or an entity associated with the individual) that the data generated from scanning the individual is/was suitable for further analysis in extracting parameters associated with CVD/HTN.

In variations, Block S110 can include providing information in any one or more of: a visual manner (e.g., with rendered information in text or graphic from within an application), an audio manner, a haptic manner, and in any other suitable manner. The information is preferably provided at an electronic device (e.g., the mobile computing device implemented in other blocks of the method 100, a personal computer, wearable computing device, tablet, etc.) of the individual, but can additionally or alternatively be provided to the individual in a non-electronic manner. Preferably, the information is provided by way of an native application executing at the mobile computing device implemented in other blocks of the method 100, including a display configured to graphically display visual and/or textual information related to the analysis. However, in variations, the information can be provided at any other suitable device and/or in any other suitable manner.

In relation to irregularities or other features of interest of the analysis, Block S110 can include sending a notification to the individual using another suitable communication channel. In one variation, the notification can be provided at a messaging client (e.g., text messaging client, email client, etc.), accessible by the individual at a mobile computing device and/or a personal computer of the individual. In another variation, the notification can be provided using a vibration motor of another electronic device of the individual. However, the notification can be provided in any other suitable manner. Furthermore, in some variations, the notification can additionally or alternatively be provided to an entity associated with the individual, in order to inform another entity of a state of the individual. In variations, the entity can be any one or more of: a parent, a sibling, a significant other, a healthcare provider, a supervisor, a peer, and any other suitable entity associated with the individual. As such, the entity can be notified regarding a health condition, related to the individual's cardiovascular health.

1.5 Method—Specific Flows

Figure 6:
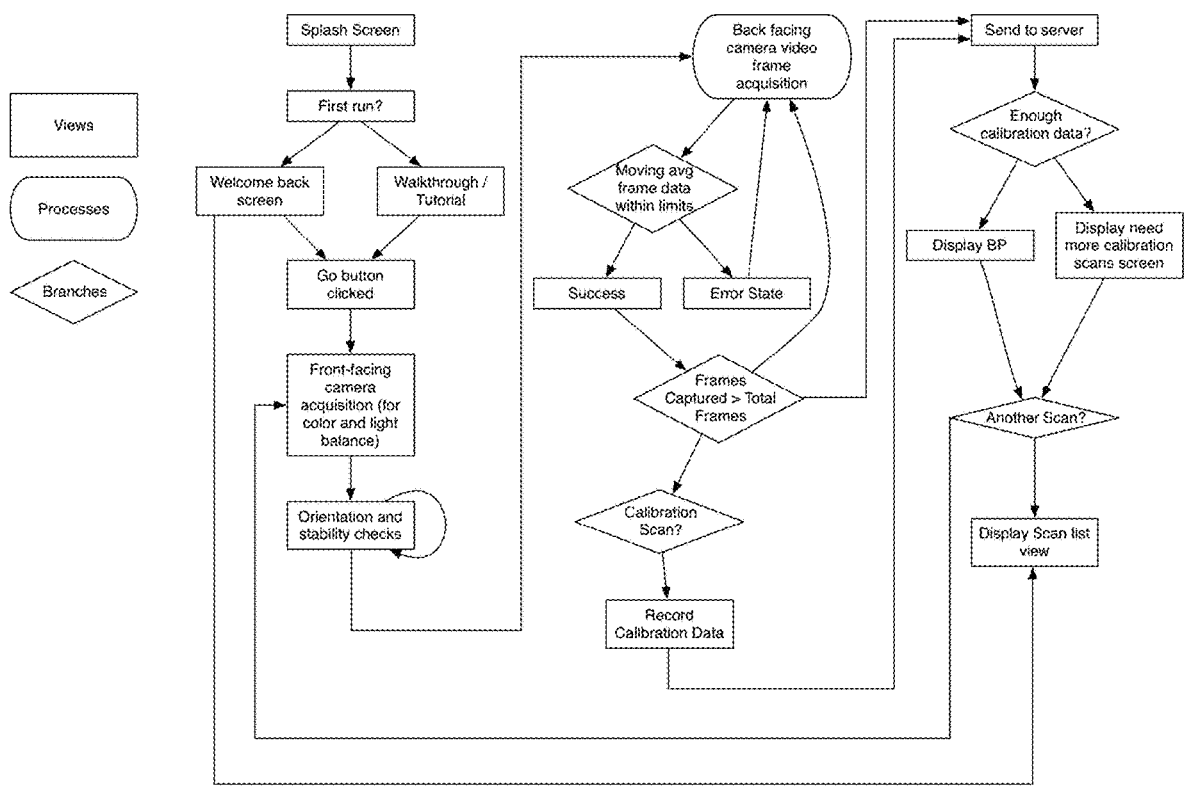
FIG. 6 depicts an example workflow of an application implementing an embodiment of a method for acquiring data for assessment and management of cardiovascular health.

As indicated above, in association with data acquisition and processing according to Blocks of the method 100, one or more signal processing operations can be performed to generate values of parameters relevant to assessment/monitoring of CVD/HTN. For instance, as shown in FIG. 6, input data can comprise the time series of image data (i.e., summed image frame data) associated with Block S110, accelerometer and gyroscope data associated with Blocks S120 and S130, ambient light data (i.e., color and light balance data) associated with Block S140, and passive location/activity data. In some variations, this input data can then be filtered to perform one or more of: bad frame removal; offset correction; trend detection/removal; color/light balance DC offset estimation; signal reconstruction; signal qualification; and any other suitable signal conditioning operation. Next, peak detection can be performed on the filtered data, wherein peak detection can comprise one or more of: bandpass selection for $1^{st}$ and $2^{nd}$ harmonics of the filtered signal; bandpass selection for $3^{rd}$ and $4^{th}$ harmonics of the filtered signal (e.g., with peak-to-peak distance constraints); determination of an area under the curve (AUC) parameter for identified peaks; peak detection qualification; and any other suitable peak detection related process. In relation to Blocks S160 and/or S165 above, the data can then be processed with one or more of: dimension reduction algorithms (e.g., K-NN algorithms, principal component analyses, isomaps, etc.); classification algorithms (e.g., unsupervised classification, supervised classification, etc.); model updating algorithms; and any other suitable analytical algorithm. One or more calibration operations (e.g., Bayesian calibration, permutation-based calibration, root-mean-square calibration error estimation) can then be performed. Finally, CVD-relevant parameters can be determined, including one or more of: a harmonics-based blood pressure parameter, a harmonics-based heart rate parameter, a time series/harmonics-based heart rate variability parameter, a blood pressure variability parameter; and any other suitable CVD-related parameter. However, variations of the specific example can include any other suitable data acquisition/analytics process.

Figure 7:
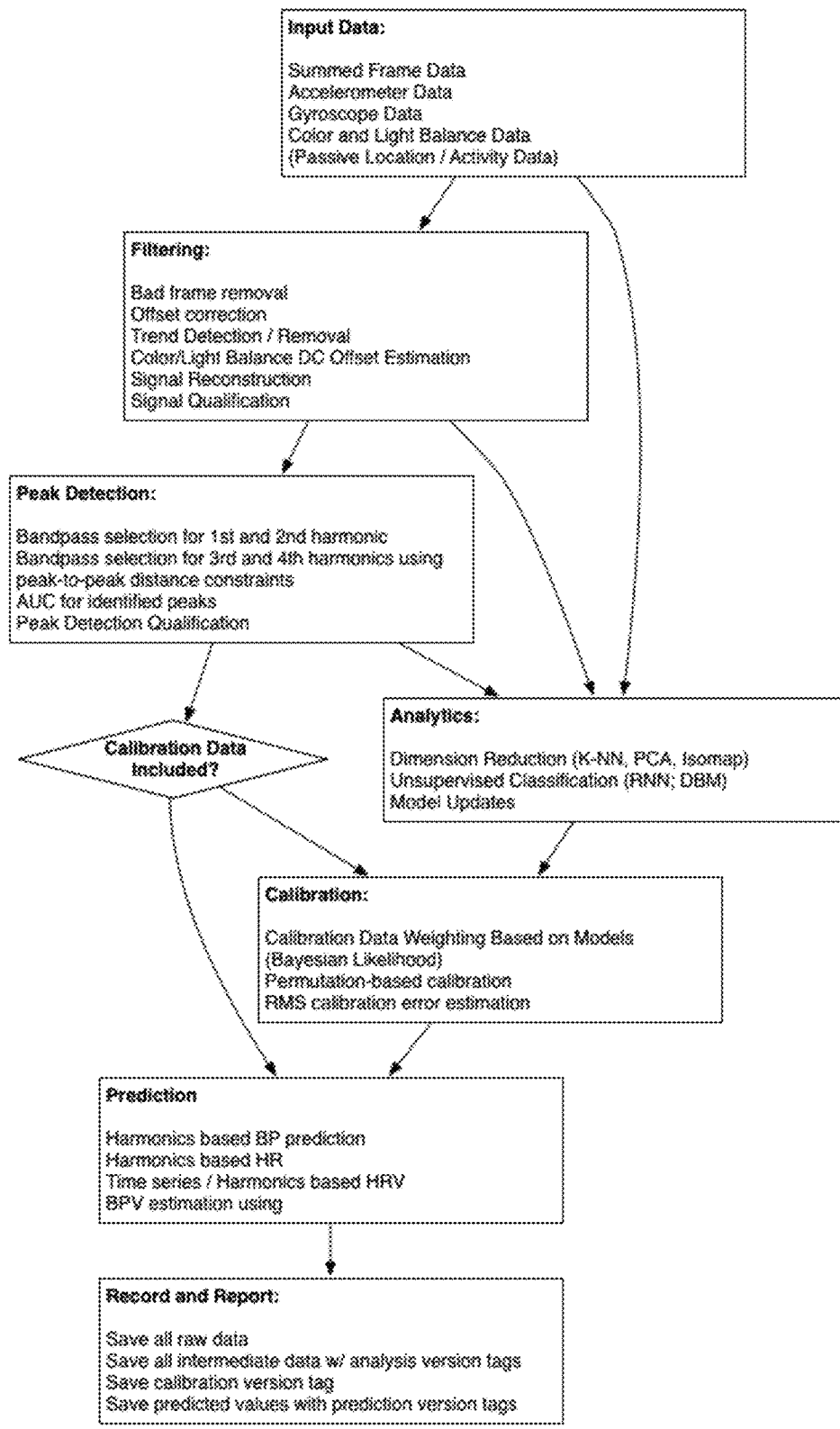
FIG. 7 depicts an example of an analytics workflow in an embodiment of a method for acquiring data for assessment and management of cardiovascular health.

In a specific application of the method 100, as shown in the flow diagram of FIG. 7, an individual can opt, within an application executing at a mobile computing device, to begin a scan, and the front-facing camera unit of the mobile computing device can begin collecting ambient light data for PPG data normalization. The individual can then be guided to modulate the orientation of the mobile computing device according to Block S120 above (for orientation and stability checks), with acquisition of image data of the fingertip region of the individual from the back-facing camera unit of the mobile computing device according to Block S110. During data acquisition, a check can be performed to determine if the moving average frame data satisfies desired limit conditions, and if a desired number of frames is captured, the data can be sent to a remote server for processing, along with any calibration data. At the remote server, if sufficient calibration data is acquired, values of CVD-relevant parameters are determined and rendered at the display of the mobile computing device by the running application. However, if insufficient calibration data is acquired, the individual can be prompted, in-application, to provide additional calibration data. Variations of the specific application of the method 100 can, however, be performed in any other suitable manner.

The method 100 can, however, include any other suitable blocks or steps configured to enhance signal quality and/or facilitate determination of values of CVD-relevant parameters. Furthermore, as a person skilled in the art will recognize from the previous detailed description and from the figures and claims, modifications and changes can be made to the method 100 without departing from the scope of the method 100.

2. System

Figure 8:
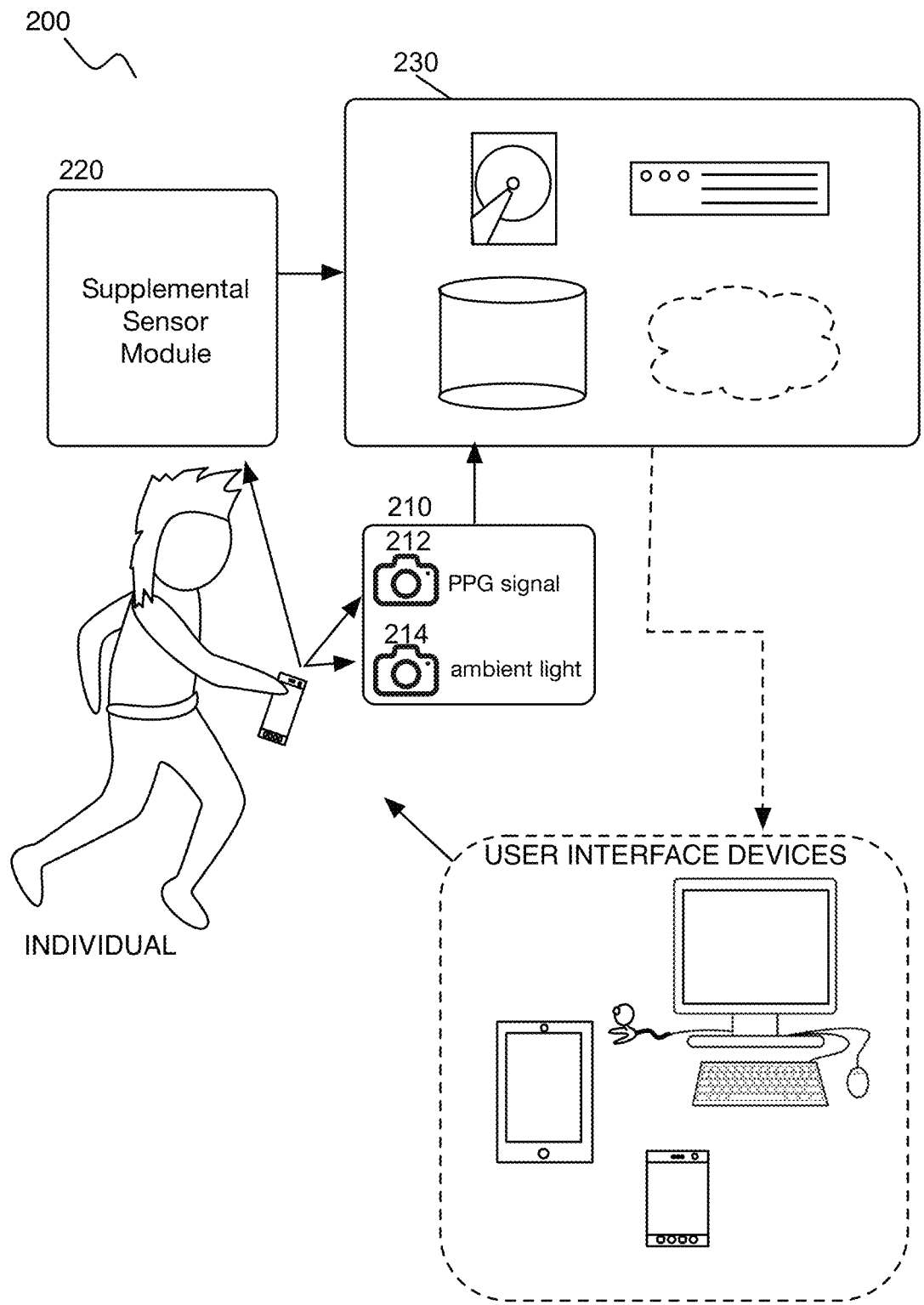
FIG. 8 depicts an embodiment of a system for acquiring data for assessment and management of cardiovascular health.

As shown in FIG. 8, a system 200 for acquiring data for assessment of CVD in an individual can include a camera module 210 including at least one camera unit 212 configured to generate a time series of image data from a body region of the individual and a second camera unit 214 configured to generate ambient light data for normalization of the time series of image data; a supplementary sensor module 220 configured to facilitate identification of a device orientation that produces a desired signal quality and to generate supplemental data; and a computing system 230 in communication with the camera module 210 and the supplementary sensor module, wherein the computing system 230 is configured to perform one or more Blocks of the method 100 described in Section 1 above.

The computing subsystem 230, as shown in FIG. 8, can be implemented in one or more computing systems, wherein the computing system(s) can be implemented at least in part in a mobile computing device, in a machine (e.g., server, personal computer, etc.) configured to receive a computer-readable medium storing computer-readable instructions, and/or in the cloud. In one specific application, a data acquisition module of the computing subsystem 230, along with user interface aspects can be implemented in a mobile computing device associated with the individual, with data processing implemented at a remote server with a graphics processing unit. The modules of the computing subsystem 230 can, however, be alternatively distributed across machine and cloud-based computing systems in any other suitable manner.

Variations of the method 100 and system 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method comprising:
   a) determining a time series of data of a body region of the individual at a device coupled to an individual;
   b) determining a mapping of the body region of the individual at the device for each of a set of frames of the time series of data;
   c) determining an active pixel set for each of the set of frames of the time series of data;
   d) aggregating at least one of the mappings or the active pixel sets of the set of frames of the time series of data into an aggregated time series of data; and
   e) determining a health biomarker value of the individual based upon the aggregated time series.

2. The method of claim 1, further comprising transmitting the health biomarker value to the device.

3. The method of claim 1, further comprising:
   iteratively repeating steps a)-e) to determine a second health biomarker value; and
   comparing the first health biomarker value to the second health biomarker value.

4. The method of claim 1, further comprising extracting a subset of the aggregated time series of data, wherein the health biomarker value is determined based on the subset.

* * * * *

UNITED STATES PATENT AND TRADEMARK OFFICE
CERTIFICATE OF CORRECTION

| | |
|---|---|
| PATENT NO. | : 12,109,050 B2 |
| APPLICATION NO. | : 18/522806 |
| DATED | : October 8, 2024 |
| INVENTOR(S) | : Tuhin Sinha et al. |

It is certified that error appears in the above-identified patent and that said Letters Patent is hereby corrected as shown below:

On the Title Page

Column 1, Related U.S. Application Data, Line 1, Delete "(60)" and insert --(62)-- therefor Signed and Sealed this
Nineteenth Day of November, 2024

Katherine Kelly Vidal
*Director of the United States Patent and Trademark Office*